United States Patent [19]

Sih

[11] 4,256,905
[45] Mar. 17, 1981

[54] 19-HYDROXY-19-METHYL-6A-CARBA-PGI$_2$ COMPOUNDS

[75] Inventor: John C. Sih, Portage, Mich.

[73] Assignee: The Upjohn Company, Kalamazoo, Mich.

[21] Appl. No.: 126,461

[22] Filed: Mar. 3, 1980

Related U.S. Application Data

[62] Division of Ser. No. 54,720, Jul. 5, 1979, Pat. No. 4,225,507.

[51] Int. Cl.$^3$ ............................................. C07C 59/11
[52] U.S. Cl. .................................................... 560/119
[58] Field of Search .......................... 560/119; 562/501

[56]  References Cited

U.S. PATENT DOCUMENTS 4,205,178   5/1980   Axen ..................................... 560/121

Primary Examiner—Robert Gerstl
Attorney, Agent, or Firm—Robert A. Armitage

[57]  ABSTRACT

The present invention provides novel 19-hydroxy-19-methyl-6a-carba-PGI$_1$ compounds which are useful for pharmacological purposes, e.g., anti-asthmatic indications.

1 Claim, No Drawings

19-HYDROXY-19-METHYL-6A-CARBA-PGI₂ COMPOUNDS

CROSS REFERENCE TO RELATED APPLICATION

The present invention is a divisional application of United States Ser. No. 054,720, filed July 5, 1979 now U.S. Pat. No. 4,225,507.

BACKGROUND OF THE INVENTION

The present invention provides novel prostacyclin analogs. Particularly, the present invention relates to prostacyclin analogs substituted at the C-19 position by hydroxy.

Particularly, the present invention relates to 19-hydroxy-19-methyl-6a-carba-PGI₂ compounds. The novel prostacyclin analogs are useful for pharmacological purposes, e.g., as anti-asthmatic agents. The preparation and use of these compounds is incorporated here by reference from U.S. Pat. No. 4,225,507, filed July 5, 1979.

PRIOR ART

For background on prostacyclin, see for example R. A. Johnson, et al., Prostaglandins 12, 915-928 (1976) and R. A. Johnson, et al., J. Am. Chem. Soc. 100, 7690-7704 (1978), and, as to pharmacological activity, the references cited therein. For analogs of prostacyclin, see, for example, J. Fried, et al., Proc. Natl. Acad. Sci. U.S.A. 74, 2199-2203, K. C. Nicolaou, et al., J.C.S. Chem. Comm. 1977, 331-332, N. A. Nelson, J. Am. Chem. Soc. 99, 7362-7363 (1977), and K. Kojima, et al., Tetra. Letters, 1978, (1977), and K. Kojima, et al., Tetra. Letters, 1978, 3743-3746. Regarding the nomenclature for analogs of PGI₂, see R. A. Johnson, et al., Prostaglandins 15, 737-740 (1978).

SUMMARY OF THE INVENTION

The present invention particularly provides a prostacyclin-type compound of the formula

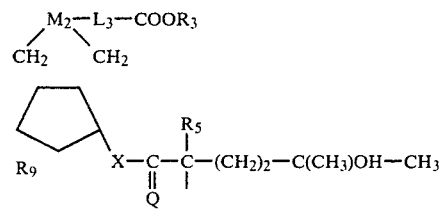

6 wherein $L_3$ is
(1) —(CH₂)ₙ—, wherein n is one to 5, inclusive,
(2) —(CH₂)ₚ—CF₂—, wherein p is 2, 3, or 4, or
(3) —CH₂—CH═CH—;
wherein $M_2$ is

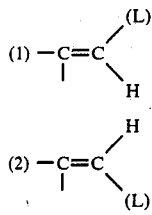

wherein Q is oxo, α-H:β-H, α-OH:β-R₄, or αR₄:β-OH,
wherein R₄ is hydrogen or alkyl of one to 4 carbon atoms, inclusive,
wherein R₃ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive;
(g) —(Ph)—CO—CH₃,
(h) —(p—Ph)—NH—CO—(p—Ph)—NH—CO—CH₃,
(i) —(p—Ph)—NH—CO—(p—Ph),
(j) —(p—Ph)—NH—CO—CH₃,
(k) —(p—Ph)—NH—CO—NH₂,
(l) —(p—Ph)—CH═N—NH—CO—NH₂,
(m) β—naphthyl,
(n) —CH₂—CO—R₁₆,
wherein —(Ph)— is inter-phenylene and —(p—Ph) is inter-para-phenylene or para-phenyl;
wherein R₁₆ is phenyl, p-bromophenyl, p-biphenylyl, p-nitrophenyl, p-benzamidophenyl, or 2-naphthyl, or
(o) a pharmacologically acceptable cation; wherein R₇ and R₈ are hydrogen, alkyl of one to 12 carbon atoms, inclusive, benzyl, or phenyl, being the same or different, and wherein R₁₅ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of one to 4 carbon atoms, inclusive, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro; wherein R₉ is hydrogen or hydroxyl; and
wherein X is
(1) trans—CH═CH—,
(2) cis—CH═CH—,
(3) —C≡C—, or
(4) —CH₂CH₂—.

I claim:
1. A prostacyclin-type compound of the formula

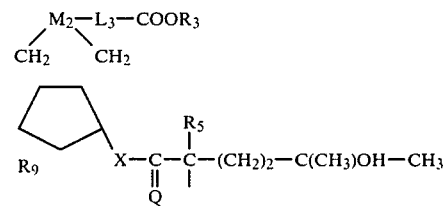

6 wherein L₃ is
 (1) —(CH₂)ₙ—, wherein n is one to 5, inclusive,
 (2) —(CH₂)ₚ—CF₂—, wherein p is 2, 3, or 4, or
 (3) —CH₂—CH=CH—;
wherein M₂ is

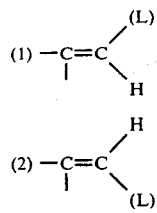

wherein Q is oxo, α-H:β-H, α-OH:β-R₄, or α-R₄β-OH, wherein R₄ is hydrogen or alkyl of one to 4 carbon atoms, inclusive,
wherein R₃ is
 (a) hydrogen,
 (b) alkyl of one to 12 carbon atoms, inclusive,
 (c) cycloalkyl of 3 to 10 carbon atoms, inclusive,
 (d) aralkyl of 7 to 12 carbon atoms, inclusive,
 (e) phenyl,
 (f) phenyl substituted with one, 2, or 3 chloro or alkyl groups of one to 3 carbon atoms, inclusive;
 (g) —(Ph)—CO—CH₃,
 (h) —(p—Ph)—NH—CO—(p—Ph)—NH—CO—CH₃,
 (i) —(p—Ph)—NH—CO—(p—Ph),
 (j) —(p—Ph)—NH—CO—CH₃,
 (k) —(p—Ph)—NH—CO—NH₂,
 (l) —(p—Ph)—CH=N—NH—CO—NH₂,
 (m) β-naphthyl,
 (n) —CH₂—CO—R₁₆,
wherein —(Ph)— is inter-phenylene and —(p—Ph) is inter-para-phenylene or para-phenyl;
wherein R₁₆ is phenyl, p-bromophenyl, p-biphenylyl, p-nitrophenyl, p-benzamidophenyl, or 2-naphthyl, or
 (o) a pharmacologically acceptable cation;
wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro;
wherein R₉ is hydrogen or hydroxyl; and
wherein X is
 (1) trans—CH=CH—,
 (2) cis—CH=CH—,
 (3) —C≡C—, or
 (4) —CH₂CH₂—.

* * * * *

UNITED STATES PATENT OFFICE
CERTIFICATE OF CORRECTION

Patent No. 4,256,905            Dated  17 March 1981

Inventor(s)  John C. Sih

It is certified that error appears in the above-identified patent and that said Letters Patent are hereby corrected as shown below:

Column 1, lines 50-60, and Column 2, lines 57-67, should read as follows instead of as appears in the printed patent:

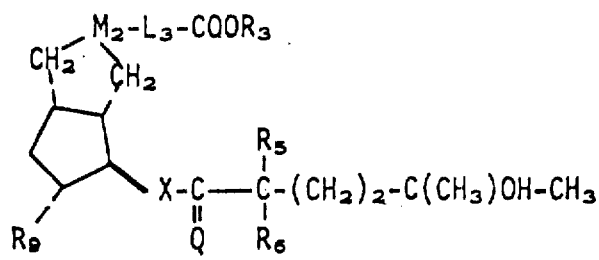

Column 2, line 11, "or $\alpha R_4:\beta$-OH" should read -- $\alpha$-$R_4$:$\beta$-OH --;
Column 3, line 18, "or $\alpha$-$R_4\beta$-OH" should read -- $\alpha$-$R_4$:$\beta$-OH --.

Signed and Sealed this

Thirtieth Day of June 1981

[SEAL]

Attest:

RENE D. TEGTMEYER

Attesting Officer      Acting Commissioner of Patents and Trademarks